United States Patent [19]

Botich et al.

[11] Patent Number: 5,188,599
[45] Date of Patent: * Feb. 23, 1993

[54] RETRACTABLE NEEDLE SYSTEM

[75] Inventors: Michael J. Botich, Oxnard; Thor Halseth, Simi Valley, both of Calif.

[73] Assignee: Med-Design, Inc., Simi Valley, Calif.

[*] Notice: The portion of the term of this patent subsequent to Feb. 19, 2008 has been disclaimed.

[21] Appl. No.: 656,305

[22] Filed: Feb. 15, 1991

Related U.S. Application Data

[63] Continuation-in-part of Ser. No. 378,275, Jul. 11, 1989, Pat. No. 4,994,034.

[51] Int. Cl.$^5$ .............................................. A61M 5/24
[52] U.S. Cl. .................... 604/110; 604/198; 604/232
[58] Field of Search ............. 604/110, 192, 194, 195, 604/197, 198, 220, 226-227, 231-232, 240

[56] References Cited

U.S. PATENT DOCUMENTS

| | | | |
|---|---|---|---|
| 2,752,918 | 7/1956 | Uytenbogaart | 604/231 X |
| 4,841,985 | 6/1989 | Wanamaker | 128/763 |
| 5,019,044 | 5/1991 | Tsao | 604/110 |
| 5,049,133 | 9/1991 | Villen Pascual | 604/110 |
| 5,053,010 | 10/1991 | McGary et al. | 604/110 |
| 5,064,419 | 11/1991 | Gaarde | 604/195 |

Primary Examiner—C. Fred Rosenbaum
Assistant Examiner—C. Maglione
Attorney, Agent, or Firm—Cislo & Thomas

[57] ABSTRACT

A hypodermic injection system (7) with a retractable needle (9) wherein the needle (9) retracts within an interior cavity (71) of a syringe plunger (59), such that the needle (9) is confinedly held within the plunger (59). A cylindrical spring housing (21) has resilient fingers (23) which captures a spring (15) biasly holding a needle holder (11) against the retaining force of resilient fingers (23). The plunger (59) has a frangible end (65), which dissociates when the outwardly tapered shoulders (68) spread the resilient fingers (23), allowing the coiled spring (15) to eject the needle (9) and its holder (11) into the interior cavity (71) of the syringe plunger (59). A body fluid sampling embodiment employs the same functional elements except the plunger (59") is shorter and contains a linking needle (137) that communicates with a vacuum container (147). The container allows fluid sampling and provides the structure to release the spring (15") retracting the needle (9").

26 Claims, 4 Drawing Sheets

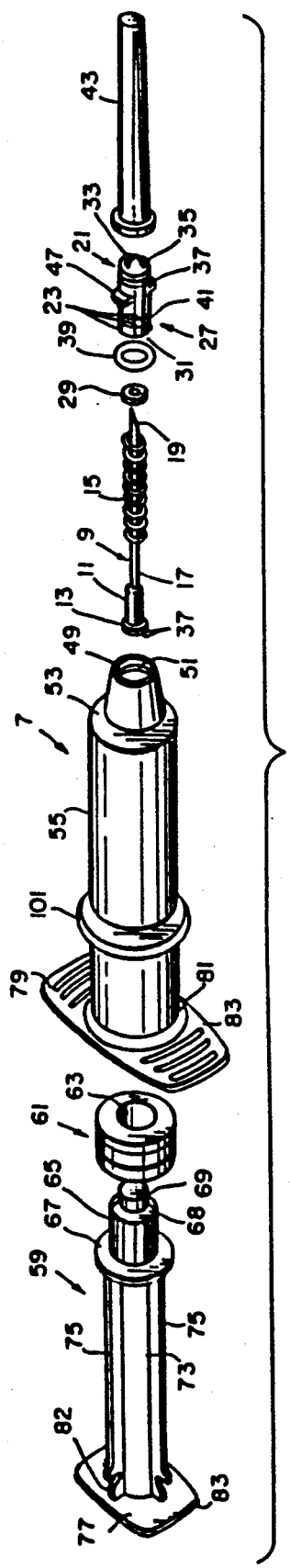

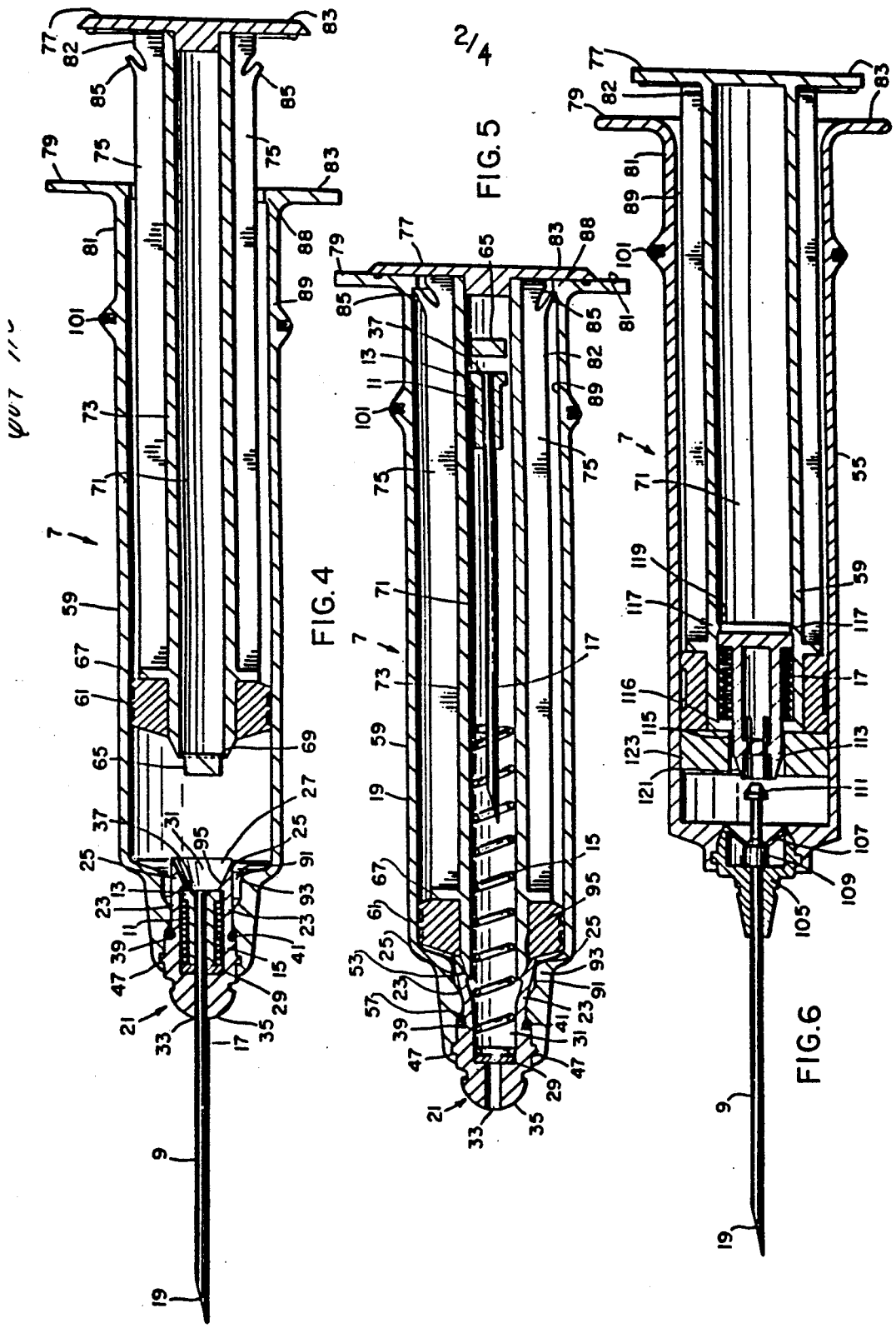

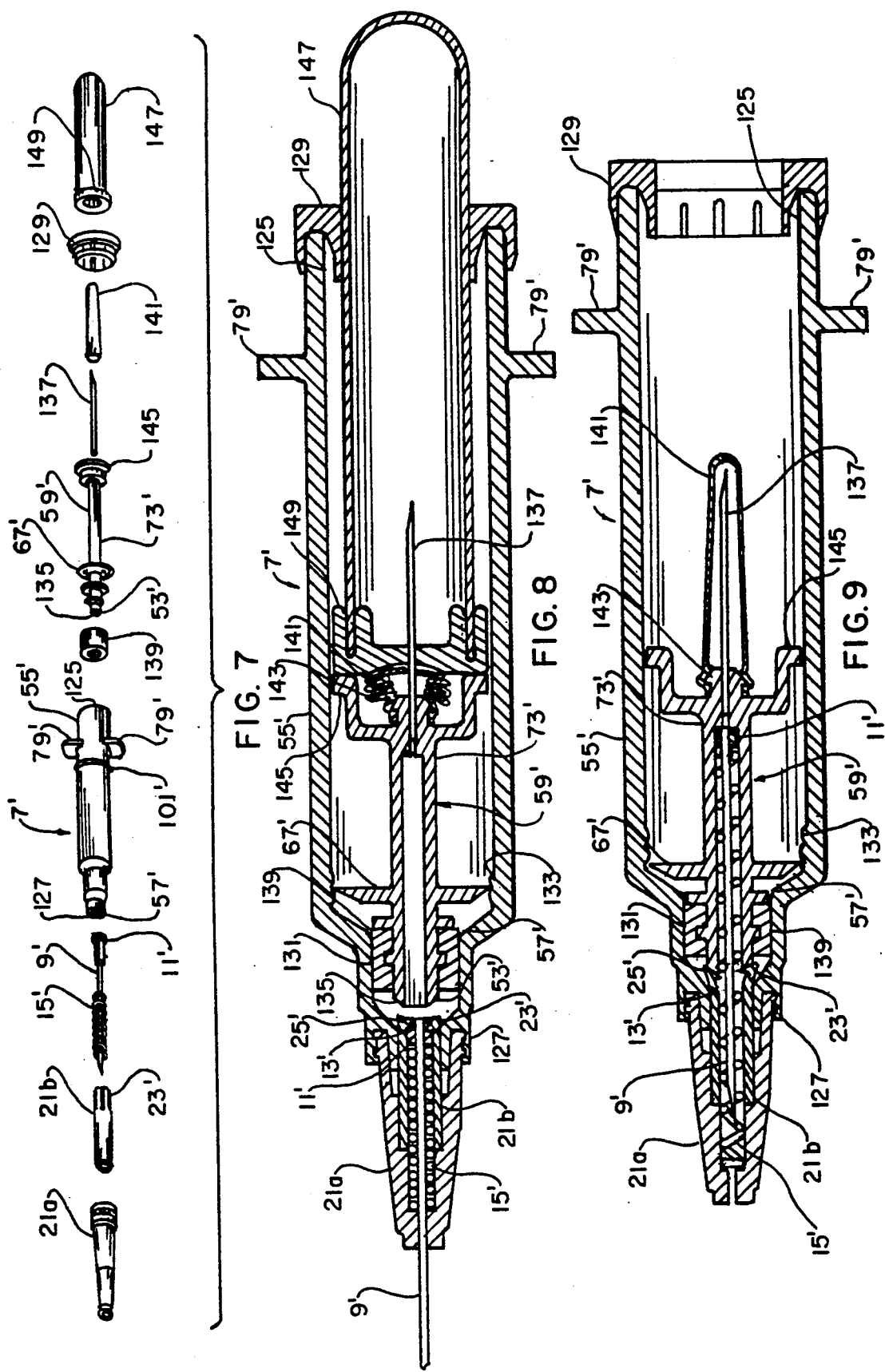

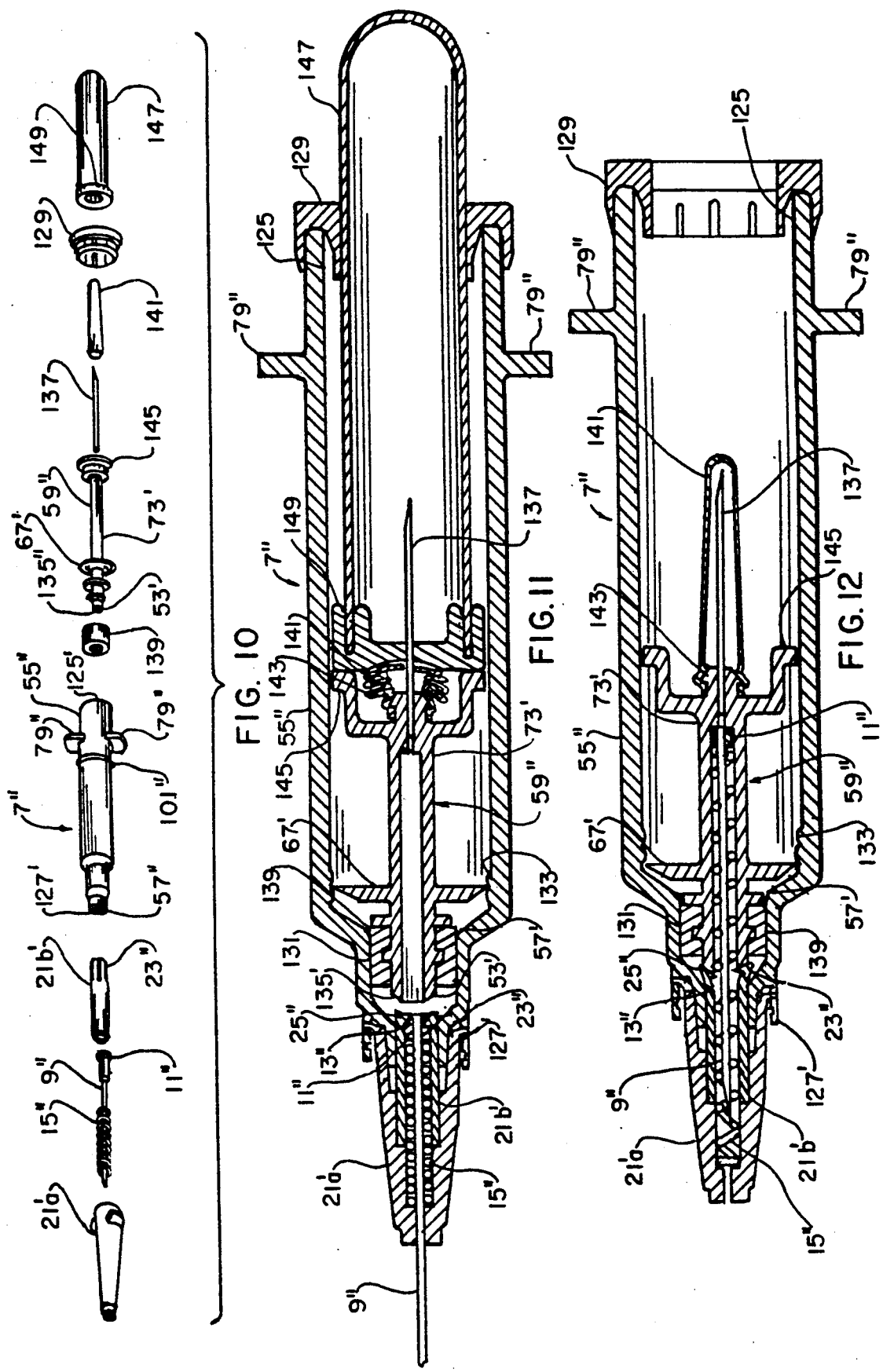

RETRACTABLE NEEDLE SYSTEM

CROSS REFERENCE TO RELATED APPLICATION

This application is a continuation-in-part of application Ser. No. 07/378,275 filed Jul. 11, 1989 and issued as U.S. Pat. No. 4,994,034 on Feb. 19, 1991.

TECHNICAL FIELD

This invention relates generally to hypodermic needle syringes and particularly to hypodermic syringes that are suited for quickly and effectively removing the sharp injection needle which poses a serious health threat.

BACKGROUND ART

Various types of hypodermic needles currently exist in the art, with the object being to provide a protective cover or cap over the possibly wound-inflicting needle. Needles found in hypodermic syringes must be very sharp to quickly and easily puncture the skin of the patient in order to provide medicinals beneath the layer of skin or remove blood for testing. Additionally, the hypodermic needle is usually very thin and hard to see, especially in low-light conditions. It is possible for doctors and nurses to accidentally prick themselves with the needle, either prior to or after an injection of a patient.

Pricking oneself prior to the injection of a solution does not present much of a health risk, since the needles to be used are normally sterilized. Also, hypodermic syringes usually come with a needle cap which is secured over the top of the needle to prevent the accidental puncturing of skin. When the doctor or nurse takes off the needle cap, exposing the needle, there is little risk of being injured by the needle. However, upon placing the needle cap back onto the needle, the fingers can be pricked by a slight visual miscalculation or by a motorneuro mistake. The consequences of this type of accident are more extreme.

Since the needle has already punctured the skin of the patient, blood and body fluid containing viruses or bacteria which may be found in the patient could possible be transferred to the health care provider by a single accidental prick.

Various types of diseases previously known could be conveyed by such an accident, including hepatitis and cholera.

In the last decade, an even more menacing and lethal virus, the Acquired Immunity Deficiency Syndrome, or AIDS virus, is easily communicated by such an accidental and catastrophic event. Since there is no known cure for AIDS at this time, a great deal of care is required to prevent the accidental prick of the health care provider by a hypodermic needle which has previously been used on a patient.

Many types of syringes of one type or another have been developed in an effort to address this problem yet allow the ease of use of more conventional hypodermic needles.

A search of the prior art did not disclose any patents that read directly on the claims of the instant invention however, the following U.S. patents were considered related:

| U.S. PAT. NO. | INVENTOR | ISSUED | |
|---|---|---|---|
| 3,046,985 | Saenz, O. | 31 July | 1962 |
| 3,134,380 | Armao, T. | 26 May | 1964 |
| 3,306,290 | Weltman, H. S. | 28 February | 1967 |
| 3,890,971 | Leeson, T. A. | 24 June | 1975 |
| 4,367,738 | Legendre, R. | 11 January | 1983 |
| 4,416,663 | Hall, R. N. | 22 November | 1983 |
| 4,631,057 | Mitchell, C. B. | 23 December | 1986 |
| 4,695,274 | Fox, R. L. | 22 September | 1987 |
| 4,702,739 | Milorad, N. M. | 27 October | 1987 |
| 4,731,068 | Hesse, J. E. | 15 March | 1988 |
| 4,735,618 | Hagen, J. | 5 April | 1988 |
| 4,737,144 | Choksi, P. V. | 12 April | 1988 |
| 4,737,150 | Baeumle, H. | 12 April | 1988 |
| 4,738,663 | Bogan, David E. | 19 April | 1988 |
| 4,743,233 | Schneider, M. | 10 May | 1988 |
| 4,747,829 | Jacob, et al | 31 May | 1988 |
| 4,747,830 | Gloyer, et al | 31 May | 1988 |
| 4,747,831 | Kulli, J. C. | 31 May | 1988 |
| 4,752,290 | Schramm, J. J. | 21 June | 1988 |
| 4,755,170 | Golden, T. A. | 5 July | 1988 |
| 4,772,272 | McFarland, B. C. | 20 September | 1988 |
| WO 89/00435 (PCT) | Gaarde, K. W. | 26 January | 1989 |

U.S. Pat. No. 3,046,985 issued to C. Saenz on Jul. 31, 1962 discloses a dental syringe adapter for concealing a needle of the hypodermic syringe prior to use by a dentist. The needle is retained in a housing until a syringe plunger is depressed and the needle is pushed out of the protective housing instead of being captively retained within a syringe body.

U.S. Pat. No. 3,134,380 issued to T. Armao on May 26, 1964 discloses a hypodermic syringe needle having a shield which need not be removed prior to the use of the needle and which can be disposed of along with the needle itself. Holes are provided near the end of the shield to permit the escape of air as the shield is collapsed allowing the needle to protrude through the protective caps. The cap is held in an extended position by a spring which yields upon injection.

U.S. Pat. No. 3,306,290 issued to H. S. Weltman on Feb. 28, 1967 discloses a retractable needle syringe which retracts the needle into a fluid containing body and not the syringe plunger.

U.S. Pat. No. 3,890,971 issued to T. A. Leeson on Jun. 24, 1975 discloses a safety syringe for one time use including a plunger which is lockable by detent members and a slidable needle cap which is also permanently lockable to prevent reuse. The needle cap slides over the exterior of the syringe barrel and over the fixed needle.

U.S. Pat. No. 4,367,738 issued to R. Legendre on Jan. 11, 1983 discloses a pre-filled syringe having spikes upon the plunger rods to prevent the withdrawal of the plunger from the syringe barrel. No means is disclosed for protecting the tip of the needle from accidental pricking.

U.S. Pat. No. 4,416,663 issued to R. N. Hall on Nov. 22, 1983 discloses a self sterilizing needle, wherein a capsule containing sterilizing fluid and having perforated ends of flexible material with elastic memory tendencies for self sealing after actual penetration by the forward end of the needle. The capsule is coaxially and slidably received over the forward end of the needle with the forward exposed end of the needle slidably penetrating one end of the capsule and perforation for sterilizing of the needle. A syringe is provided for axially urging and positioning the capsule outward to its original position of rest. Then, the exposed end of the needle is again enclosed in the capsule for sterlization when the hypodermic penetration force is removed.

U.S. Pat. No. 4,631,057 issued to C. B. Mitchell on Dec. 23, 1986 discloses a needle coupled to a syringe barrel, wherein a needle guard is mounted on the barrel for movement from a retracted position in which the guard does not shield the needle to an extended position in which the guard shields the needle.

U.S. Pat. No. 4,695,274 issued to R. L. Fox on Sep. 22, 1987 discloses a safety needle attachment wherein the needle is initially and entirely surrounded by a protecting jacket which is releasably interlocked with a holder. When the needle is to be used, an interlocker is released and the jacket is effectly telescoped over the holder to project the needle through a membrane over the end of the jacket to a working position.

U.S. Pat. No. 4,702,739 issued to N. M. Milorad on Oct. 27, 1987 discloses a hypodermic needle having a sleeve extending from a holder protectively covering the needle so that the sleeve can be placed against the body part where injection is to occur and with the needle tip end proximate the body part. By sliding the holder toward the body part a detent restraint holding the sleeve in an extended position is overcome and relative retraction movement effected therewith.

U.S. Pat. No. 4,731,068 issued to J. E. Hesse on Mar. 15, 1988 discloses a non-reloadable syringe wherein the plunger is permitted to be withdrawn for purposes of loading the syringe and permitted to be urged forward to discharge the contents of the syringe. However, means is provided wherein subsequent retraction of the plunger assembly is inhibited to prevent further loading and use of the syringe.

U.S. Pat. No. 4,735,618 issued to J. Hagen on Apr. 5, 1988 discloses a protective enclosure for a hypodermic syringe needle formed by a tubular sleeve sized for friction fitting engagement over the barrel portion of the syringe. A needle guard portion is located at an opposed end and pivotally removable arms operate to permit the needle to pass through a central channel of the needle guard.

U.S. Pat. No. 4,737,144 issued to P. V. Choksi issued Apr. 12, 1988 discloses a syringe system comprising a tubular barrel and a sleeve mounted on the barrel to slide lengthwise from a retracted position in which the needle is exposed, and an extended position in which the sleeve extends protectively about the needle.

U.S. Pat. No. 4,737,150 issued to H. Baeumle on Apr. 12, 1988 discloses a tube-cannula syringe, the first cannula being disposed so as to be displaced relative to the second cannula to be removable or displaceable in the longitudinal direction of the syringe.

U.S. Pat. No. 4,738,663 issued to David E. Bogan on Apr. 19, 1988 discloses a sleeve guide having a pair of fasteners with cavities formed in them that fit over the flange which are located on hypodermic syringes for grasping in the user's fingers. The guide in the retracted position prevents the accidental pricking by the needle.

U.S. Pat. No. 4,743,233 issued to Michael B. Schneider on May 10, 1988 discloses a slidable sleeve over a syringe barrel that is connectable in a first position extending over a hypodermic needle and that is reconnectable in a second position along the syringe barrel to expose the needle for use.

U.S. Pat. No. 4,747,829 issued to J. Jacob et al on May 31, 1988 discloses a pre-filled syringe with a retractable needle. A barrel of the syringe is removable within a casing from a remote pre-injection position to a forward injection position and back again. The barrel is moved forward allowing the needle to pass through an opening in a cap prior to injection.

U.S. Pat. No. 4,747,380 issued to W. W. Gloyer et al on May 31, 1988 discloses a syringe having a hollow barrel formed at the distal end to receive an injection piston carried by the plunger member which allows the needle to also to retract within the barrel by extracting the piston.

U.S. Pat. No. 4,747,831 issued to John C. Kulli on May 31, 1988 discloses a cannula insertion needle housing. The housing includes a latch mechanism for extending the needle and retracting the needle.

U.S. Pat. No. 4,752,290 issued to J. J. Schramm on Jun. 21, 1988 discloses a tubular shield which is adapted to protect users from injury. The tubular shield cooperates with the raised surfaces on the body of the medical appliance to be protected.

U.S. Pat. No. 4,755,170 issued to T. A. Golden on Jul. 5, 1988 discloses a protective sealing device comprising a block with which a sharp end of the needle can be held within to prevent accidental puncture. Also, disclosed is a retaining shield which can be retracted over the needle to prevent accidental puncture.

U.S. Pat. No. 4,772,272 issued to B. C. McFarland on Sep. 20, 1988 discloses a protective sleeve for a hypodermic needle which sleeve is completely dissociable from the hypodermic syringe. The protective sleeve is moved over the needle protecting position to the needle injection position solely by axially movement of the protective sleeve.

An International Patent Application filed by K. W. Gaarde and having a published number WO 89/00435 and a publication date of Jan. 26, 1989 shows a hypodermic syringe with a retractable needle in a needle holding mechanism which is integrally attached to a syringe body.

It is desirable that the hypodermic needle can be made available in a safe condition prior to injection so that the health care provider will not accidentally prick his finger and require a new sterilized needle prior to the injection of the patient. It is also a requirement that after injection or sampling using the hypodermic needle, that the needle can be safely and easily discarded without representing a continued health risk to anyone who may encounter the hypodermic needle, either on the premises of the health care facility, or in transit or arrival at the refuse collection area or dump.

There is potentially a great interest in the health care industry to manufacture, sell, distribute and use a hypodermic needle and a vacuum tube syringe that provides the type of safety as described above. It can be easily operated, provides to be completely reliable and is easily and cheaply manufactured, yet still has a great deal of versatility for various applications using various needles in diameter and length and different sized vacuum tubes.

The features described above as being desirable above for hypodermic syringes and vacuum tube syringes are all provided for by the present invention.

DISCLOSURE OF THE INVENTION

The present invention is embodied in an approved hypodermic syringe system which is entirely safe prior to injection or sampling due to a protective cover tip. Furthermore, after injection or sampling, the hypodermic syringe system is entirely safe, since the health care provider, using one hand, can retract the needle into a tamperproof isolation container which may then be easily and safely discarded, preventing the injury or transmission of any dangerous viruses or bacteria. In addition, the hypodermic syringe system is easily manufactured, easy to use and provides visual and audible confirmation that the needle has been safely retracted after use.

More particularly, the hypodermic injection system comprises a cylindrical syringe housing assembly, holding a retractable injection needle which can be safely, quickly, and easily retracted within a specially designed syringe plunger. Furthermore, the plunger is fixedly held after use within a specially designed syringe barrel. The syringe barrel, plunger and needle assembly can be easily discarded without the dangers associated with an exposed needle or needle that can be easily uncapped. The needle is held locked inside the barrel which is tamperproof.

In a more specific description of the invention, the injection needle has a sharp end, a shaft with an axial passageway therethrough, and a holder defining a raised plastic lip seal. The injection needle is mounted within a cylindrical spring housing assembly having frangible and resilient fingers which are spreadable radially outward on a first end and extending tabs that extend radially outward on an external surface of the cylindrical needle housing. Thus, a mechanism is provided for associating the cylindrical spring housing with the syringe barrel in a locking manner. Once the needle assembly is fully threaded, any attempt to unscrew the needle assembly is impeded by a one way locking finger on the needle housing. The cylindrical spring housing includes a first sealing means for providing a seal between the cylindrical spring housing and the holder of the hypodermic injection needle. Also, a second sealing means for providing a seal between the cylindrical spring housing and the syringe barrel is used.

An opening in a second end of the cylindrical spring housing is sized to receive the shaft of the injection needle while retaining the holder when both are forwardly positioned within the cylindrical spring housing assembly. The frangible and resilient fingers of the spring housing have radially inwardly positioned hooks sized to engage and hold the raised sealing lip of the holder of the injection needle when the shaft of the injection needle is forwardly located within the cylindrical spring housing. The hooks have inwardly tapered shoulders so as to be easily spread by complementing and outwardly positioned tapered shoulders of the syringe plunger.

A coiled spring is positioned axially within the cylindrical spring housing assembly between the holder and the second end of the cylindrical spring housing. The spring exerts an expansive force between the holder of the injection needle and the second end of the cylindrical spring housing, a force which is less than the retaining force exerted by the hooks of the frangible and resilient fingers, thereby retaining the injection needle within the cylindrical spring housing against the expansive force of the spring.

The syringe barrel includes helical threads sized and positioned to receive the extending locking tabs of the cylindrical spring housing and the second sealing means to provide a pressure tight seal between an interior tapered surface of the cylindrical spring housing and an exterior tapered wall of the barrel. The interior of the barrel is shaped sufficient to engage the cylindrical spring retainer and allow the resilient legs to flex radially outward or the frangible fingers to fracture and then resiliency flex outwardly.

The syringe plunger is sized to be received concentrically within the syringe barrel and has a hollow, axially located chamber therein. The syringe plunger has a frangible end plug located within outwardly tapered shoulders adjacent to the chamber. The frangible end plug disassociates from the syringe plunger upon contact with the needle holder and is injected into the hollow chamber when the outward tapered shoulders forcibly engage the inwardly tapered shoulders of the hooks of the frangible and resilient fingers, thereby spreading the fingers outwardly and disengaging the hooks from the raised lip of the holder of injection needle. The frangible end dissociates under a pre-determined normal force between the holder of the injection needle and the frangible end. This allows the coiled spring to eject the syringe needle from the cylindrical spring housing into the chamber within the plunger.

Optionally, the chamber located within the syringe plunger may be evacuated so that when the frangible end breaks and ejects with the needle into the chamber, any peripheral fluid is also drawn into the chamber and away from the cylindrical spring housing.

Furthermore, an outwardly-oriented ring or lip on the exterior of the plunger is positioned so as to engage a complementing recess or slot within the interior of the syringe barrel when the plunger is in a fully-depressed position to lock the plunger within the syringe barrel, preventing its removal and access to the retained needle therein.

The holder of the needle can have a bright color (such as red) so as to be visually distinctive within the transparent syringe barrel and syringe plunger, so that the health care provider can readily determine that the syringe is in a safe condition for transport or discard. The exterior of the syringe barrel can also be fitted with a color-coded sizing ring, which quickly and clearly identifies the size or capacity of the syringe system.

In a second embodiment, the needle ejecting mechanism can be held on the end of the syringe plunger. In that configuration, the needle is retained by a frangible needle holder associated with the ejection end of the syringe barrel. The hypodermic needle has a head which can be readily grabbed by a modified end of the syringe plunger. Depression on the syringe plunger dissociates the needle from the frangible needle holder. Further depression on the syringe plunger allows a needle retractor to pass by engaging detents, while a similar coiled spring ejects the needle retractor which is now engaging the needle, ejecting the needle into the interior chamber of the syringe plunger.

A third embodiment of the invention uses the same principles as the preferred embodiment except the attachment of the spring housing is slightly different and the hollow end in the plunger is larger. Other minor differences simplify the structure somewhat.

In a fourth embodiment for taking blood samples, the barrel is basically the same along with the hypodermic needle with the holder and the coiled spring. The plunger however, is much shorter and contains a hollow linking needle on the inside end. A standard sampling fluid vacuum container is inserted into the barrel and impinges on the linking needle through a resilient cap like seal creating a flowpath for the blood sample through the hypodermic injection needle. When the sample has filled the container, the extending end is forced into the barrel with the user's thumb. The tapered end of the plunger forceably spreads the resilient fingers holding the injection needle outward releasing the needle against the expansive force of the coiled spring. This action permits the spring to extend into the hollow syringe plunger retracting the needle inside as in the preferred embodiment.

The hypodermic syringe system of the present invention provides for a retractable needle which is durable, disposable, easy to manufacture, prevents the accidental pricking after use, and provides for greater ease of handling the hypodermic needle after use, including the subsequent discarding of the device. The hypodermic needle is extremely simple in construction, yet completing effective in injecting fluid below the skin or taking blood samples, subsequently becoming completely safe after use while the health care provider need only use one hand to retract the needle, leaving his other hand free. Furthermore, his or her fingers may remain in their relative positions to retract the needle.

Other aspects and advantages of the present invention will be apparent from the following description of the preferred embodiments, taken in conjunction with the accompanying drawings, which illustrate, by way of example, the principals of the invention.

BRIEF DESCRIPTION OF THE DRAWINGS

FIG. 1 is an exploded view of the hypodermic syringe of the present invention.

FIG. 2 is a partial cross-sectional view of the hypodermic syringe of the present invention shown with its plunger proximate to the needle housing.

FIG. 3 is a cross-sectional view of the hypodermic syringe of the present invention with the needle housing, needle, and needle cap shown exploded from the syringe barrel.

FIG. 4 is a cross-sectional view of the hypodermic syringe in the present invention shown with the syringe plunger in a partially depressed position within the syringe barrel.

FIG. 5 is a cross-sectional view of the hypodermic syringe of the present invention shown with the syringe plunger in a fully depressed position and the needle fully retracted.

FIG. 6 is a cross-sectional view of the second embodiment of the hypodermic syringe of the present invention.

FIG. 7 is an exploded view of the hypodermic syringe in the third embodiment.

FIG. 8 is a cross-sectional view of the hypodermic syringe of the third embodiment of the present invention shown with the plunger open ready for use.

FIG. 9 is a cross-sectional view of the hypodermic syringe of the third embodiment of the present invention with the plunger in the fully depressed position and the needle fully retracted.

FIG. 10 is an exploded view of the hypodermic syringe in the vacuum tube blood sampling embodiment.

FIG. 11 is a full cross-sectional view of the hypodermic syringe in the vacuum tube blood sampling embodiment shown with the vacuum tube installed in the device and the hypodermic needle extended ready for use and the cap removed.

FIG. 12 is a full cross-sectional view of the hypodermic syringe in the vacuum tube blood sampling embodiment with the tube removed and the needle retracted ready for disposal.

BEST MODE FOR CARRYING OUT THE INVENTION

The best mode for carrying out the invention is presented in the terms of a preferred, second, third and fourth embodiment. All four embodiments are basically identical in principle and function, however, slight variations in structure segregate the four. The preferred embodiment is shown in FIGS. 1–6, wherein like numerals represent like elements throughout, the complete hypodermic syringe 7 of this embodiment is best shown in exploded view as FIG. 1. The main components of syringe 7 are a standard injection needle 9 having a specially-mounted holder 11 including an enlarged lip 13, located posteriorly thereto. A coiled spring 15 rides a shaft 17 of the injection needle 9 with an axially located passageway 19 therethrough. A cylindrical spring housing 21 includes a plurality of radial spaced resilient fingers 23 which include inwardly engaging an inferiorally positioned hooks 25 on the posterior end 27 of the spring housing 21. A sealing means or washer 29 is sized to be received within an inner cavity 31 of the spring housing 21.

The injection needle 9, including the enlarged lip 13 of the holder 11 can be forwardly positioned within the inner cavity 31 of the cylindrical spring housing 21. A cross-shaped opening 33 in a forward end 35 of the spring housing 21 allows the shaft 17 of the injection needle 9 to extend through the cross-shaped opening 33. The enlarged lip 13 is engaged by the hooks 25 when forwardly positioned within the spring housing 21, causing the resilient fingers 23 and hooks 25 to flex around the enlarged lip 13 and engage a top surface 37 of the enlarged lip 13.

The washer 29 provides a secure seal between the shaft 17 of the injection needle 9 and the inner cavity 31 of the spring housing 21. Finally, a gasket or o-ring 39 engages a circumferential groove 41, located midway between the posterior end 27 of the spring housing 21 and the forward end 35 of the spring housing 21. This configuration can be more clearly shown in FIG. 2, and also in FIG. 3, partially exploded from the other components of the hypodermic syringe 7 of the present invention.

Also, shown in FIG. 3 is a needle cap 43, which engages a forwardly-positioned second circumferential groove 45 of the spring housing 21. The spring housing 21 has radially-extending bayonet slots 47, which provide locking engagement within bayonet slots 49 and a bayonet groove 51, located within a tapered nose 53 of a syringe barrel 55. Engagement between the spring housing 21 and the tapered nose 53 of the syringe barrel 55 is easily accomplished by aligning the bayonet tabs 47 with the bayonet slots 49 and pushing the spring housing 21 through the bayonet slots 49 and then rotating the bayonet tabs 47 within the bayonet groove 51 to provide locking engagement therebetween. The bayonet tabs 47 may have slanted edges (not shown) on opposing sides and the bayonet groove may have raised surfaces (not shown) to allow the slanted edges to pass by the raised surface in one direction of rotation. This effectively locks the spring housing 21 to the tapered nose 53 of the syringe barrel 55 in a racket-like manner.

The first tapered inner wall 57 within the tapered nose 53 of the syringe barrel 55 provides sealing engagement between the spring housing 21 and the syringe barrel 55, due to the tight fit of the o-ring 39 between the spring housing 21 and the first tapered inner wall 57.

A plunger 59 is sized to be received within the syringe barrel 55 and engages a plunger piston 61 of a conventional type commonly used with syringe systems known in the art, except that a cylindrical cavity 71 extends therethrough, allowing a frangible end 65 to enter the cylindrical cavity 71 of the plunger piston 61. The plunger piston 61 is positioned over the associated frangible end 65 and is supported by a rim 67. The length of the plunger piston 61 is such that outwardly tapered shoulders 68 extend through and above the passageway 63 of the plunger piston 61, joining the frangible end 65. Between the outwardly tapered shoulders 68 and the frangible end 65 is a circumferential groove 69 of a defined thickness of approximately 0.031 inches (0.080 cm) which allows the frangible end 65 to dissociate from the outwardly tapered shoulders 68 upon a normal force on the frangible end 65 of approximately two pounds or less in the preferred embodiment. The circumferential groove 69 can, of course, simply be a thinner construction of material allowing frangibility.

The plunger 59 includes the cylindrical central cavity 71 running axially through the plunger 59 and adjacent to the frangible end 65. The cylindrical cavity 71 has a diameter sufficient to allow the enlarged lip 13 and the holder 11 and the associated shaft 17 of the injection needle 9 to be injected into the cylindrical cavity 71 and need not be circular. Furthermore, the cylindrical cavity 71 can be evacuated so as to allow the vacuuming effect upon the dissociation of the frangible end 65 from the outwardly tapered shoulder 68.

A plunger sleeve 73 defines the cylindrical cavity 71 while reinforcement ribs 75 provide support to the plunger sleeve 73 and are associated with the rim 67 to provide additional support when the plunger 59 is being depressed. A pushing plate 77 is located on a posterior end 82 of the plunger 59. The pushing plate 77 is sized sufficient to allow the thumb of a normal person to properly depress the plunger 59 when associated with the syringe barrel 55.

Also, finger retaining lips 79 are associated with the posterior end 81 of the syringe barrel 55 so as to allow the index finger and middle finger to grasp the finger-retaining lips 79 of the syringe barrel 55 while the thumb presses upon the pushing plate 77. Grooves 83 or knurling may be etched within the finger-retaining lips 79 or upon the pushing plate 77 to provide a greater coefficient of friction between the fingers and thumb and the finger retaining lip 79 and pushing plate 77, respectively.

Radially extending ratchet teeth 85 interrupt the reinforcing ribs 75 and are posteriorly located while being posteriorly flared to allow the ratchet teeth 85 to pass by an extending ratchet lip 88 defined by an interior wall 89 of the syringe barrel 55. Upon full depression of the syringe plunger 59 within the syringe barrel 55, the ratchet teeth 85 pass by the ratchet lip 88. The ratchet teeth 85 flexibly pass by the ratchet lip 88 and prevent the extraction of the plunger 59 from the syringe barrel 55.

In operation, the syringe 7 of the instant invention, functions very much like a conventional hypodermic syringe as found in the prior art. However, after injection, of the substance to be injected the hypodermic syringe 7 of the instant invention allows the dissociation of the frangible end 65 from the outwardly tapered shoulders 68 of the plunger 59 and the radial flexing of the resilient fingers 23 so that the hooks 25 release the enlarged lip 13 of the holder 11 of the injection needle 9.

Since a circumferential space 91 exists between the resilient fingers 23, and the inner wall 93 of the syringe barrel 55, the resilient fingers 23 can flex, releasing the holder 11. The resilient fingers will only flex when inwardly tapered surfaces 95 of the hooks 25 are engaged by the outwardly tapered shoulders 68 of the plunger 59. Such engagement takes place when the plunger 59 is pushed through the syringe barrel 55 and the frangible end 65 abuts against the top surface 37 of the holder 11. A normal force of less than 2 pounds exerted between the top surface 37 of the holder 11 and the frangible end 65 causes the frangible end 65 to dissociate from the outwardly tapered shoulders 68 of the plunger 59.

With the resilient fingers 23 flexed radially outward, causing the hooks 25 to release the holder 11, the compressed spring 15 exerts an ejecting force against the enlarged lip 13 of the holder 11, propelling the injection needle 9 along with the holder 11, as well as the dissociated frangible end 65 into the cylindrical cavity 71 of the plunger 59.

The above operation makes a very distinctive click sound alerting the health care provider that the device is now safe.

Also, if the cylindrical cavity 71 is evacuated, a suction pulls any residual fluids into the cylindrical cavity 71. Upon further depression of the syringe plunger 59 into the syringe barrel 55, the ratchet teeth 85 engage the ratchet lip 88, preventing the plunger 59 from being extracted from the syringe barrel 55.

The holder 11 can be a bright red or fluorescent color, while the plunger 59 and syringe barrel 55 can be manufactured from a transparent or translucent material so that the retracted position is readily identified in low light conditions and the needle is visibly safe for further handling, transport or discard.

Also, an interchangeable identification ring 101 can be positioned around the syringe barrel 55 so as to identify the hypodermic syringe 7 for whatever purpose.

The plunger 59, syringe barrel 55, holder 11, spring housing 21 and needle cap 43 can be made from a transparent or translucent plastic material. However, the spring housing 21 does not necessarily have to be transparent nor does the holder 11. Such materials and their manufacturer are well known in the art and will not be further herein described. The plunger piston 61 can be formed of a neoprene material sufficient to provide a seal between the plunger piston 61 and the syringe barrel 55 and is also commonly known in the art and will not be hereinafter described in more detail. The shaft 17 of the injection needle 9 is of material known in the art as well.

The o-ring 39 can be of a elastomeric material, just as the washer 29 may also be of a resilient material, so as to provide a proper sealing effect well known in the art. It should be noted that the spring housing 21 must be formed of a durable plastic material which is resilient, so that the resilient fingers 23 properly and radially outwardly extend in association with the syringe plunger 59. The syringe plunger must be of a more resilient or brittle material or have a proper thickness so as not to flex inwardly when the frangible end 65 dissociates from the plunger 59. It is important that the plunger 59 remains sufficiently durable to cause the resilient fingers 23 to move radially outward when the inwardly tapered surfaces 95 of the hooks 25 engage the outwardly tapered shoulders 68 of the syringe plunger 59. Specific examples of types of plastics and thicknesses are not required, as these can be readily determined by those ordinarily skilled in the art of plastics manufacture.

In the second embodiment, the mechanism responsible for ejecting the injection needle 9 can be fully positioned within the syringe plunger 59. As shown in FIG. 6, some slight variations in structure are necessary to achieve results similar if not identical to as described in the first embodiment of the invention.

The injection needle 9 is held within a frangible needle holder 105, which includes a frangible cone 107, which engages an enlarged section 109 of the injection needle 9. The injection needle 9 has a length sufficient to extend well within the syringe barrel 59 and has an extraction end 111, which can be engaged by extraction hooks 113 of similar design as shown in FIGS. 1-5.

A needle retractor housing 115 is located and held on an inward end of the syringe plunger 59, specifically held in place by detents 117, defined within the interior wall 119 of the cylindrical cavity 71 of the plunger 59. The compressed spring 17 exerts force between the needle retracting housing 115 and the inner end 116 of the plunger 59. The force exerted by the spring is not sufficient to force the needle retractor housing 115 past the detents 117.

In operation the plunger 59 is pushed into the barrel 55 having outwardly tapered shoulders 121, which break the frangible cone 107, thereby releasing the enlarged section 109 of the injection needle 9. Further downward pressure on the plunger 59 forces the needle retractor housing 115 past detents 117, allowing the spring 15 to expand, pushing the needle retractor housing 115 deep within the cylindrical cavity 71 and taking with it the injection needle 9, because the hooks 113 grab the extraction end 111 as the needle retractor housing 115 is moved deeper into the cylindrical cavity 71 of the plunger 59. It should be noted that an extra piston spacer 123 is required for proper operation, due to the injection needle 9 extending within the syringe barrel 55.

Besides the above-identified differences, the second embodiment of the invention functions substantially as the first and the materials necessary for each of the components are similar to those materials as described in the first embodiment of the invention.

The third embodiment of the invention is illustrated in FIGS. 7-9 and consists of a syringe barrel 55' having a partially open end 125 and a fully opened end 127. The barrel 55' has finger retaining lips 79' on the partially opened end 125 providing a gripping surface for the user's fingers. Optionally, near the lips 79', a color coded ring 101 of sufficient resilience and diameter is slid over the exterior surface of the barrel 55' and retained by friction to identify the particular syringe system. The open end 127 of the barrel contains bayonet slots 49' and grooves 51' or threads for connecting other elements to the open end. The barrel 55' is transparent thus, permitting the user to see the fluid inside allowing expulsion of bubbles of air that may be within the liquid dispensed by the syringe.

A hollow syringe plunger 59' is slidably received within the barrel 55' and is sized to move linearly back and forth without restriction. The plunger 59' has a converging taper 135 on one end and an axial flange 136 on the other. The flange 136 has a radially thinned slender section 138 at the interface with the barrel 55' which actually breaks away if forced outwardly when the plunger 59' is in its fully closed position contiguous with the barrel 55'.

A resilient barbed stopper 140 is tightly pressed into the flange end of the plunger 59' completely closing the end thereof allowing a hermetic seal inside the plunger. A frangible end 65' is located on the tapered end 135' of the plunger 59' completing the hermetic seal inside. The plunger 59' further contains an outwardly extending raised circumferential band 142 around the flange end and the barrel 55' has an internal recessed girdle 144 in a similar location near the lips 79'. When the plunger 59' is fully depressed and is recessed flush with the end of the barrel 55', the band 142 snaps into the recessed girdle 144 locking the plunger 59' into place. This prevents the plunger from being withdrawn and as the flange 136 is frangible, the closure becomes tamper-proof even if an attempt is made to pry the flange 136 from the barrel 55'.

On the converging tapered end 135 of the plunger, a piston 61' is positioned over a raised radial projection 146. This piston is resilient in nature and seals the internal portion of the barrel 55' allowing liquids to be drawn inside and forced out by the movement of the plunger 59'. Initially, the piston 61' is located such that it is forward of the tapered end 135, however, when the plunger 59' is fully inserted into the barrel 55', the piston 61' is forced over the radial projection 146 into a secondary position sealing tightly against the inside of the hollow of the barrel 55' and exposing the tapered end 135 of the plunger 59'.

An injection needle 9' is positioned into the partially opened end 127 of the barrel 59'. This needle 9' has an axial passageway inside and is sharp on the exposed end and flat on the other, or holder end. Spring holding means in the form of a holder 11', coiled spring 15' and spring housing 21' retain the needle 9' and attach combined elements to the barrel 55'. The holder 11' has a raised lip 13' on the end and the spring housing 21 is divided into two pieces 21a and 21b that are pressed together. The front portion 21a attaches to the barrel with bayonet tabs 47' into the threads consisting of slots 49' and grooves 51' and partially retains the spring 15'. The rear portion 21b retains the balance of the spring 15' and fingers 23' and hooks 25' are integrally formed therein in a frangible manner. The needle holder 11' is held in place as the lip 13' interfaces with the hooks 15' on the fingers 23' maintaining compressive tension on the spring 15'.

In operation, the fluid medication or pharmaceutical is drawn into the syringe 7' in a normal manner by the vacuum created when the plunger 59' is withdrawn. After injecting the liquid and the needle is withdrawn, the plunger 59' is forced completely into the barrel 55'. As the tapered end 135 of the plunger approaches the end of the hollow barrel 55', the piston 61' is forced back over the raised projection 146 and simultaneously, the plunger converging taper end 135 forceably breaks the frangible section between the resilient fingers 23' of the rear portion 23b of housing 21'. This forceable bending outward of the resilient fingers 23' releases the holders raised lip 13' held by the hooks 25 at the end of the fingers 23'. This releasing movement permits the expansive force of the coiled spring 15' to break the frangible end 65' of the plunger 59' and drive the needle 9', frangible end 65' and spring 15' into the hollow of the syringe plunger 59' fully retracting the needle 9' and retaining it safely inside the syringe 7'. An audible clicking sound is heard when this action takes place. As previously described, the plunger 59' is fully inserted into the barrel 55' with the flange 136 flush with the open end 125 of the barrel 55' and is unremovable due to the locking into place of the band 142 into the girdle 144. As it is seen, the elements and function of this embodiment are basically the same with only slight differences in structure to accomplish secondary operable features.

In a fourth embodiment of the invention, the injection needle retracting mechanism is basically the same and the functional principal is identical except that instead of using the syringe 7" for injecting fluids such as intramuscular absorbing medication or intravenous pharmaceuticals, the invention is directed to removing fluid sample such as blood from the body. The usual method to accomplish this procedure is to employ a system that includes a hypodermic needle and a barrel including a interconnecting needle that pierces a vacuum container or vial drawing the sample into the container when the connection is made. The same problem exists with this system as it exposes a sharp hypodermic needle with only a removable cover for protection. The inside interconnecting needle is of little danger as it is completely surrounded by the barrel and is unaccessible to most parts of the medical practitioner's body, at least without a conscious effort.

The invention's embodiment for a device used in taking body fluid samples is illustrated in FIGS. 10-12 and consists of the same hypodermic needle 9", holder 11", coiled spring 15", spring housing 21" complete with resilient fingers 23" and hooks 25" and all of the associated elements. The syringe barrel 55" and the plunger 59" however, differ somewhat in structure but retain the basic function.

The syringe barrel 55" is cylindrical in shape and has a fully open end 125' and an opposed partially opened end 127'. The open end 125' may optionally contain a replaceable centering washer 129 that fits over the end 125' and that has a predetermined inside diameter allowing a single barrel to be used with various diameter fluid sampling receptacles. Finger retaining lips 79" are positioned away from the end 125' in this embodiment serving to assist the user in handling and manipulating the device and allowing the washer 129 to be installed on the extreme end 125'. The partially opened end 127' of the barrel contains the same tapered nose 53' and tapered inner wall 57' except a straight reduced bore section 131 is added extending the end slightly. On the inside surface of the barrel 55", near the partially opened end 127', are located a pair of circumferential snap release projections 133 that have a slightly smaller inside diameter, a radial shape, and that are positioned parallel and close to one another. These projections 133 are integrally formed with the plastic barrel 55" and function as a retainer for the operating parts described later.

The material of the barrel 55" may be opaque or translucent, however, transparent is preferred to allow the sampling vial to be viewed when it is disposed within. Additionally, a color-coded identifying ring 101" may be slid over the exterior surface of the barrel 55" and be retained by a slide fit to identify the size of the syringe system such as its needle diameter, length, etc.

A hollow syringe plunger 59" is slidably received within the barrel 55". This plunger is configured to contain a converging taper 135' on one end and a hollow linking needle 137 on the other. The plunger's tapered end 135' includes a resilient seal 139 that snaps over the plunger and becomes a closure between the plunger 59" and in the straight reduced bore section 131 creating a tight hermetic seal with sufficient resistance to maintain the seal when slid linearly in the bore.

The linking needle 137 is held within the plunger 59" through a compression fit and is parallel with the inside of the barrel 55" as shown in FIGS. 11 and 12. A needle boot 141 is disposed over the needle 137 and stretches over a barbed projection 143 integral with the plunger holding the needle 137 on the inside and providing a gripping surface for the boot. The boot 141 is formed of a thin resilient material such as flexible silicone and is sized to enclose and protect the needle when stored.

The needle end of the plunger 59" further contains an offset extended flange 145 almost the same diameter as the inside of the barrel 55" creating a stop and centering the plunger in the barrel.

The middle portion of the plunger 59" is considerably smaller in diameter than the barrel and defines a hollow plunger sleeve 73' with a rim 67' near the tapered end 135'. This rim 67' is basically the same structure as the preferred embodiment except the outer edge is tapered sharply permitting the tip of the rim 67' to be held in place between the peripheral snap release projections 133 located inside the barrel 55". When the plunger 59" is urged toward the partially open end 125' of the barrel, the rim 67' has sufficient resiliency to overcome its captivity between the projections and snap away from the containment. A similar snap action takes place when it is originally installed.

A sampling fluid vacuum container 147, vial or "B-D VACUTAINER" as it is sometimes known in the medical field is inserted inside the open end 125' of the barrel 55". The container 147 has a resilient perforatable seal 149 on one end and is domed shape on the other much like a test tube. The container 147 is well known in the art and widely used to receive and store body fluid samples. The container is normally fabricated of glass or transparent thermoplastic and is evacuated on the inside allowing the fluid to displace the vacuum eliminating the problem of expelling trapped air.

The spring holding means associated with and positioned on the barrel 55" is as previously described using the same hypodermic needle 9", holder 11", and coiled spring 15". The spring housing 21" is slightly different and is preferably formed in two pieces that are pressed together. The front portion 21a' interfaces with the partially open end 125' of the barrel 55" and holds part of the spring 15"; the rear portion 21b' of the housing retains the balance of the spring 15". The fingers 23" and hooks 25" are also integrally formed with the rear portion 21b'.

In operation, the container 147 is inserted loosely into the barrel 55" and the hypodermic needle 9" is inserted, usually intervenously into the patient. The container 147 is urged forward into the barrel 55" where the linking needle 137 pierces the container seal 149 and the vacuum within draws the fluid into the container. The container 149 may be removed and replaced if another sample is required however, when finished, the container is urged further into the barrel 55" toward the partially open end 127' by the practitioner thumb while grasping the lips 79" with the fingers. This compressive force overcomes the resistance of the snap release projections 133 holding the extended flange 67' allowing the plunger 59" to slide forward. The plunger converging tapered nose end 53' forceably spreads the resilient fingers 23" of the rear portion 21b' of the housing 21"

radially outward to release the holder's raised lip 13". Thus, permitting the expansive force of the coiled spring 15" to break the frangible end 65' and extend the needle 9" and holder 11" into the hollow syringe plunger 59". This triggered movement fully retracts the needle 9" into the hollow center of the plunger 59' and retains it in that position by the continual urging of the coiled spring 15" thus repositioning the needle 9" into a permanently protected and harmless location. An audible clicking sound is emitted when this action is completed and the container 147 may then be removed. Any liquid on the needle is again harmlessly retained inside the syringe 7" and disposal may be safely achieved. A color coded ring 101" as shown in FIGS. 1 and 4-6, may optionally be used in this embodiment if desired.

It should be appreciated from the foregoing description that the present invention describes an improved hypodermic syringe with a retractable needle which is simple in construction, yet completely effective in retracting a needle once the needle has served its purpose in the injection or removal of fluids below the surface of the skin. The hypodermic syringe of the present invention can be conveniently assembled from a minimum number of separate parts, all of which can be manufactured with relatively inexact precision, all of which are configured to facilitate compact and efficient operation. The hypodermic syringe of the present invention can be fully and safely operated by the use of one hand to retract the needle and allow for safe handling, transport and discard.

Although the present invention has been described in detail with reference only to the presently-preferred embodiment, it will be appreciated by those of ordinary skill in the art that various modifications can be made without departing from the invention. Accordingly, the invention is limited only by the following claims.

We claim:

1. A hypodermic syringe system comprising:
   (a) a syringe barrel including a nose section disposed at one end,
   (b) a syringe plunger including an interior cavity and a frangible end adjacent thereto an, said syringe plunger sized to be received within and slide through said syringe barrel,
   (c) an injection needle, and
   (d) a spring holding means readily associable and attachable to said syringe barrel, for holding said injection needle and selectively retracting said injection needle into said interior cavity of said syringe plunger when said syringe plunger abuts against and moves beyond a portion of said syringe barrel, causing breakage of said frangible end, and allowing said frangible end of said syringe plunger to separate, wherein said spring holding means comprises; a holder for holding said injection needle; and a spring means for exerting an expansive force between said holder and said spring holding means, wherein said spring holding means selectively holds said holder and said spring means therebetween while allowing said injection needle to extend through said spring holding means in an assembled condition wherein said holder has a lip, said spring holding means has extending resilient fingers with interior and inferiorly positioned hooks to retain said lip of said holder in an assembled condition wherein, said fragible end of said syringe plunger has an engaging and complementing surface which abuts up against said hooks of said extending resilient fingers, spreading said extending resilient fingers radially outwardly to release said lip against the expansive force of said spring means when said syringe plunger moves beyond said portion of said syringe barrel, and wherein said spring holding means attachable to said syringe barrel and lockable thereto, preventing removal of said spring holding means from said syringe barrel.

2. The hypodermic syringe system as specified in claim 1 wherein said frangible end of said syringe plunger separates when a predetermined normal force is exerted between said frangible end of said syringe plunger and said holder.

3. The hypodermic syringe system as specified in claim 2 wherein said frangible end of said syringe plunger spreads said extending resilient fingers radially outward upon depression of said syringe plunger past said predetermined point within said syringe barrel prior to exertion of said predetermined normal force allowing said frangible end to dissociate and said spring means to propel said holder and injection needle into said interior cavity of said syringe plunger.

4. The hypodermic syringe system as specified in claim 1 wherein said spring holding means operatively associates with the nose section of said syringe barrel.

5. The hypodermic syringe system as specified in claim 4 wherein said interior cavity of said syringe plunger is evacuated prior to the separation of said frangible end from said syringe plunger.

6. The hypodermic syringe system as specified in claim 1 further comprising ratchet means for engaging said syringe plunger within said syringe barrel, preventing separation of said syringe plunger from said syringe barrel after said syringe plunger is depressed within said syringe barrel.

7. The hypodermic syringe system as specified in claim 6 wherein said spring holding means includes at least one extending tab and wherein said nose section of said syringe barrel includes at least one interior axial slot adjoining an inner radial slot, both sized to receive said tab and allow secure engagement between said spring holding means when associated with said nose section by positioning said tab through said axial slot and rotating said tab within said radial slot, thereby securing said spring holding means to said nose section.

8. The hypodermic syringe system as specified in claim 7 wherein said spring holding means has a frustoconical head, an axial bore through said head, of a sufficient diameter to receive said injection needle therethrough and a cylindrical exterior tapered end sized to seal against tapered interior walls of said nose section of said syringe barrel and provide sealing engagement between said spring holding means and said nose section.

9. The hypodermic syringe system as specified in claim 8 wherein said holder is a highly visible color and wherein said syringe plunger and said syringe are made of a translucent or transparent material to allow viewing said holder when ejected into said syringe plunger through said syringe barrel.

10. The hypodermic syringe system as specified in claim 9 wherein said head of said spring holding means includes an engagement groove for engagement with a needle cap.

11. The hypodermic syringe system as specified in claim 10 comprising a color-coded ring of sufficient diameter to slide over an exterior surface of said syringe barrel and be retained thereby to identify the syringe system.

12. A hypodermic syringe system comprising a captured needle a spring loaded needle means for holding and ejecting soul captured needle, barrel means for holding injectable fluid therein and connectable to said spring loaded needle means on one end, and a plunger means having a hollow portion, said plunger means positionable within and movable through said barrel means, said plunger means having a breakable end adjacent said hollow portion which breaks free from one end of said plunger means and allows said captured needle to be ejected into said hollow portion of said plunger means within said barrel means, wherein said spring loaded needle means has a housing with resilient fingers on one end, which can be spread radially outward by said one end of said plunger means in contact therewith to release said captured needle from said housing, wherein said breakable end of said plunger means breaks allowing said captured needle to be propelled out of said housing and into said hollow portion of said plunger means and be retained therein, wherein said breakable end of said plunger means includes tapered shoulders which engage oppositely and complementing shoulders of said resilient fingers, allowing forward movement of said plunger means to spread said resilient fingers radially outward, said syringe system further comprising an extending tab and a receiving slot associated between an exterior of said plunger means and the interior of said barrel means, said extending tab and said receiving slot oriented to lock together when said tab and said slot are brought into alignment with each other within said barrel means, thereby locking said plunger means within said barrel means.

13. The hypodermic syringe system as specified in claim 12 wherein said plunger means and said barrel means are substantially transparent, said captured needle having a distinctive appearance to be readily seen through said syringe plunger means and said barrel means once ejected into said plunger means.

14. The hypodermic syringe system as specified in claim 13 wherein said plunger means includes an evacuated chamber to extract fluid from said spring loaded needle means upon the dissociation of said breakable end of said plunger means.

15. A retractable needle system comprising:
(a) an injection needle having a shaft with an axial passageway therethrough, said shaft having a sharp end and a holder defining a lip on another end,
(b) a spring housing having an exterior surface, resilient legs spreadable radially outward on a first end, said spring housing having exteriorly located attachment tabs extending radially outward, an opening on a second end of said spring housing to receive said shaft of said injection needle in sealing engagement while retaining said holder, said resilient legs having radially inwardly positioned hooks sized to engage and hold said lip of said holder of said injection needle when said shaft of said injection needle is forwardly positioned within said spring housing, said hooks having inwardly tapered shoulders,
(c) a coiled spring means positioned axially within said spring housing between said holder and said second end of said spring housing, said spring means exerting a repulsive force between said holder of said injection needle and said second end of said spring housing less than the retaining force exerted by said hooks of said resilient legs, thereby retaining said injection needle within said spring housing against said repulsive force of said spring means,
(d) barrel means for engaging and holding said spring housing, said barrel means including slots and a groove sized and positioned within an interior of said barrel means to receive said extending tabs of said spring housing in locking engagement, said interior of said barrel means shaped sufficient to engage said spring housing and allow said resilient legs to flex radially outward; and
(e) a plunger sized to be received concentrically within said barrel means, said plunger having a hollow axially located chamber therein, and having a dissociable end and outwardly tapered shoulders adjacent to said dissociable end, wherein said dissociable end dissociates from said plunger and is ejected into said chamber when said outward tapered shoulders forcibly engage said inwardly tapered shoulders of said hooks of said resilient legs, spreading said resilient legs outwardly and disengaging said hooks from said lip of said injection needle, thereby allowing said dissociable end to dissociate under a predetermined normal force between said holder of said injection needle and said dissociable end, and allowing said coiled spring means to eject said injection needle from said spring housing into said chamber within said plunger.

16. A retractable needle system comprising:
(a) a barrel having an attachment end,
(b) a plunger including an interior cavity and a dissociable end adjacent thereto said plunger sized to be received within and slide through said barrel,
(c) a hollow needle; and
(d) a spring holding means including a spring, said spring holding means associated with and held by said attachment end of said barrel, for holding said needle and selectively retracting said needle into said interior cavity of said plunger when said plunger abuts against said spring holding means and moves beyond a portion of said barrel, causing dissociation of said dissociable end, and allowing said dissociable end of said plunger to separate, and wherein said spring holding means can easily be attached to said attachment end of said barrel and lockable thereto.

17. A syringe or sampling system comprising:
(a) a barrel having an attachment end;
(b) a plunger including an interior cavity and a dissociable end adjacent thereto, said plunger sized to be received within and slide through said barrel, and having a slideable piston retained on an interior end, slideable along a predetermined length,
(c) a hollow needle; and
(d) a spring holding means including a spring, said spring holding means associable with and holdable by said attachment end of said barrel, for holding said needle and selectively retracting said needle into said interior cavity of said plunger when said plunger abuts against said spring holding means and moves beyond a portion of said barrel, causing dissociation of said dissociable end, and allowing said dissociable end of said plunger to separate, while said slideable piston rearwardly slides from a first forward position to a second rearward position, and wherein said spring holding means attachable to said barrel means.

18. A retractable needle system comprising:
(a) a barrel having a partially open end and a fully opened end,
(b) a plunger, having a hollow portion and a converging taper with a resiliently slideable piston on one end, slideably received within said barrel
(c) a plunger dissociable end adjacent the converging taper end of said plunger,
(d) a needle positioned within the partially opened end of the barrel, said needle having an axial passageway therethrough, a sharp end and a holder end, and
(e) spring holding means associable with and positionable on said syringe barrel, and having a coiled spring surrounding said needle for exerting and expansive force between the holder end and the holding means, wherein the spring holding means selectively holds the holder end and the spring therebetween and further having extended resilient fingers with interior and inferiorly positioned hooks engageable with said holder end in an assembled condition, the retractable needle system safely retracting said injection needle by urging the plunger completely into the barrel toward the partially open end until the plunger dissociable end forcibly dissociates and spreads the resilient fingers of the spring holding means radially outward releasing the holder end against the expansive force of said coiled spring separating the plunger dissociable end and permitting the plunger dissociable end, the spring, the needle and its holder end to extend into the hollow portion of the plunger retracting and retaining the injection needle therewithin.

19. A blood extraction or injection system comprising:
(a) a barrel having a partially open end and a fully opened end,
(b) a plunger having a hollow portion slideably received within said barrel having a converging taper with a resilient piston on one end and a axial flange on the other,
(c) a stopper fixably disposed within said hollow portion at the flange end forming a seal,
(d) a plunger dissociable end adjacent the converging taper end of said plunger,
(e) an injection needle positioned into the partially open end of the barrel, said needle having an axial passageway therethrough, a sharp end and a holder end having a lip, and
(f) spring holding means associated with and positionable on said barrel, and having a coiled spring surrounding said needle for exerting an expansive force between the holder end and the spring holding means, wherein the spring holding means selectively holds the holder end and the spring therebetween and further having extended resilient fingers with interior and inferiorly positioned hooks engageable with said lip to retain the lip on the holder end in an assembled condition, the system safely retracting said injection needle by urging the plunger completely into the barrel toward the partially open end until the plunger's dissociable end forcibly dissociates and spreads the resilient fingers of the spring holding means radially outward releasing the lip of the holder end against the expansive force of said coiled spring and permitting the dissociable end, the spring along with the needle and holder end to extend into the hollow portion of the plunger retracting and retaining the injection needle therewithin.

20. The blood extraction or injection system is specified in claim 19 further comprising an outward extended raised circumferential band around said plunger near the flange end, said barrel having an internal recessed girdle complementary with the band positioned such that the band snaps into and locks the plunger into place when it is completely inserted into the barrel preventing the plunger from being withdrawn, also said axial flange on the plunger having a radially thinned slender section permitting the flange to break away if forced onward maintaining the integrity of the plunger position when the band is interfaced with the recessed girdle assuring the inaccessibility of the injection needle within the plunger.

21. The blood extraction or injection system as specified in claim 19 wherein said barrel is made of a transparent material to allow viewing of the liquid within when drawn into the barrel by the plunger.

22. The blood extraction or injection system as specified in claim 19 further comprising a color-coded ring of sufficient diameter to slide over an exterior surface of said barrel and be retained thereby to identify the system.

23. A retractable needle system for taking body fluid samples comprising:
(a) a barrel having a partially open end and a fully opened end,
(b) a plunger having a hollow portion slideably received within said barrel having a converging taper with a resilient piston on one end and a hollow linking needle fixably attached on the other end,
(c) an injection needle positioned onto the partially open end of the barrel, said needle having an axial passageway therethrough, a sharp end and a holder end having a lip,
(d) a sampling fluid vacuum container having a resilient perforatable seal on one end, slideably disposed within said barrel and impinged upon said linking needle such that communication is made between the container and the injection needle through the plunger allowing body fluid to be drawn into the container by vacuum for fluid sampling, and
(e) a spring holding means associated with and positionable on said barrel, said spring holding means having a coiled spring surrounding said needle for exerting an expansive force between the lip of the holder end and the spring holding means wherein the spring holding means selectively holds the holder end against the spring while allowing the injection needle to extend through the spring holding means in an assembled condition, and further having extended resilient fingers with interior and inferiorly positioned hooks engageable with said lip to retain the holder end and the needle in an assembled condition, the system safely retracting said injection needle after a sample of body fluid has been drawn into the vacuum container by urging the container further into the barrel toward the partially open end with the plunger converging tapered end forcibly spreading the resilient fingers of the spring holding means radially outward releasing the lip against the expansive force of said coiled spring permitting the spring to extend into the hollow portion of the plunger retracting the injection needle therewithin.

24. The retractable needle system as specified in claim 23 further comprising a pair of circumferential snap release projections disposed within the syringe barrel located in such a manner so as to engage and retain a portion of the plunger therebetween providing a fixed location for the plunger and yet sufficiently diminutive to allow the plunger to move forwardly toward the partially open end of the barrel by the vacuum container for retracting the injection needle.

25. The retractable needle system as specified in claim 23 wherein said spring holding means in s highly visible color and wherein said syringe barrel is made of a transparent material to allow viewing said vacuum container when disposed within said syringe barrel.

26. The retractable needle system as specified in claim 23 further comprising a color-coded ring of sufficient diameter to slide over an exterior surface of said syringe barrel and be retained thereby to identify the syringe system.

* * * * *